United States Patent [19]
Kizaki et al.

[11] Patent Number: 5,249,471
[45] Date of Patent: Oct. 5, 1993

[54] SEALING STRUCTURE FOR TESTING VESSEL

[75] Inventors: Minoru Kizaki; Masao Ohmi, both of Ibaraki; Masaaki Yokoi, Yokosuka; Shouji Yoshikawa, Tokyo, all of Japan

[73] Assignee: Japan Atomic Energy Research Institute, Tokyo, Japan

[21] Appl. No.: 831,061

[22] Filed: Feb. 4, 1992

[30] Foreign Application Priority Data

Feb. 8, 1991 [JP] Japan .................... 3-17378

[51] Int. Cl.⁵ .............................. G01N 3/08
[52] U.S. Cl. ...................... 73/826; 220/211
[58] Field of Search ............ 73/865.6, 826, 828, 73/834; 220/211, 315, 318, 324, 320, 319; 206/305, 306, 524.8; 215/274, 276, 354, 356; 374/49, 57, 51

[56] References Cited

U.S. PATENT DOCUMENTS

| | | | |
|---|---|---|---|
| 2,225,448 | 12/1940 | Hamilton | 220/315 |
| 2,877,921 | 3/1959 | Grim | 220/211 |
| 2,955,452 | 10/1960 | Myers | 220/211 |
| 4,102,473 | 7/1978 | Draxler | 220/319 |

FOREIGN PATENT DOCUMENTS

0178334 9/1985 Japan .......................... 374/9

OTHER PUBLICATIONS

Rylands Complete Specification, Jun. 1890.

*Primary Examiner*—Robert Raevis
*Attorney, Agent, or Firm*—Shapiro and Shapiro

[57] ABSTRACT

The present invention provides a sealing structure for a testing vessel, comprising a lid member secured to a base and having an upwardly projecting insertion portion and a supporting portion; a cylindrical container detachably mountable on the lid member in an up-and-down direction, the container having a lower open end portion to which said projection can be mated and which can be supported by the supporting portion and on which a plurality of first radially outwardly extending locking portions and first notches are alternately formed along a circumference thereof; a clutch member which is attached to the base and rotatingly guided in an circumferential direction by a guide member and on which a plurality of second radially inwardly extending locking portions and second notches are alternately formed within the same angular range as that of the first locking portions and first notches; and an elevator means for lowering and lifting the container to mount and dismount the latter with respect to the lid member. Wherein, when the first or second locking portions are aligned with the second or first notches by rotating the clutch member, the container can be mounted on or dismounted from the lid member by lowering or lifting the container by means of the elevator means, and the container is non-detachably attached to the lid plate when the first locking portions are engaged by the second locking portions.

1 Claim, 1 Drawing Sheet

SEALING STRUCTURE FOR TESTING VESSEL

BACKGROUND OF THE INVENTION

1. Field of the Invention

The present invention relates to a sealing structure for a testing vessel, and more particularly, it relates to an improved sealing structure for a testing vessel wherein test pieces which are made radioactive by neutrons can be tested even under special circumstances.

2. Related Background Art

In general, as to a various kinds of materials used with systems in an atomic power equipment, which are influenced upon the radiation, the detrioration of the material such as deformation and/or damage thereof due to the irradiation thereto must be grasped. To this end, test pieces made of the material having the same property as that of the material to be used are subjected to the radiation in the nuclear reactor, and various strength tests are carried out regarding the irradiated test pieces. Such strength tests are sometimes carried out under the vacuum condition or under the high pressure condition, and thus, in the past, testing vessels of sealing type have been used.

The testing vessel of this type generally comprises a cylindrical testing vessel body having an open upper end and a closed bottom end, and a lid plate covering the open upper end. When the test is carried out, the lid plate is rested on a flange formed on the upper end of the vessel body and is sealingly tightened against the vessel body by means of a tightening means such as bolts to seal the interior of the vessel body from the outside.

In the above-mentioned testing vessel, when the test piece is made radioactive, an operator cannot directly conduct operations with respect to the testing vessel, but must conduct operations with remote control, for example, by using a manipulator, from the outside of the shielded room. In this case, however, it takes a long time and labor to mount and dismount the lid plate with respect to the vessel body with the remote control, thus worsening the operability and efficiency of the test. Therefore, in order to improve the efficiency of the test, the easy and simple opening and closing operation of the lid plate has been requested.

SUMMARY OF THE INVENTION

The present invention aims to eliminate the above-mentioned conventional drawback, and has an object to provide a sealing structure for a testing vessel wherein the mounting and dismounting of a lid plate with respect to a vessel body can be performed easily and positively with remote control.

The above object can be achieved by the present invention providing a sealing structure for a testing vessel, wherein, in place of the mounting and dismounting of a lid plate with respect to a vessel body (container) as in the conventional techniques, a vessel body can be mounted on and dismounted from a fixed lid plate, and there is provided a clutch member which can be engaged by the vessel body mounted on the lid plate and which can also be disengaged from the vessel body by rotating the clutch member by small extent.

More particularly, the lid plate (20) has an upwardly projecting insertion portion (22) and a supporting portion (24) and is attached to a base (60) installed at a fixed position. On the other hand, the vessel body or container (10) has an open lower end mated with the insertion portion of the lid plate and supported by the supporting portion, and a plurality of first locking portions (16) and first notches (17) are alternately formed on a lower portion of the container within a predetermined angular range.

The clutch member (44) attached to the base is provided with a plurality of second locking portions (48) and second notches (49) radially extending and alternately arranged within the same angular range as that of the first locking portions and the first notches of the container. Further, the clutch member is rotatably guided in a circumferential direction by means of a bearing (45) disposed between the clutch member and the base and a guide member (52) secured to the base. The container is lifted and lowered (in an up-and-down movement) by elevators (66, 72) to be connected to and disconnected from the lid plate.

With this arrangement, the container can be mounted on or dismounted from the lid plate by lifting or lowering the container by means of the elevators in a condition that the first or second locking portions are aligned with the second or first notches by the rotation of the clutch member; and the container is non-detachably locked to the lid plate by engaging the first locking portions by the second locking portions.

According to the present invention, the clutch member engageable by the container and rotated with remote control, and the elevators secured to the container and adapted to automatically lift and lower the container are adopted. Thus, the operator is not obliged to be at the container's side at all times, and, even when radioactive test pieces are set within the testing vessel, the container can be mounted on and dismounted from the lid plate easily, quickly and safely.

DETAILED DESCRIPTION OF THE PREFERRED EMBODIMENT

The present invention will now be explained in connection with a preferred embodiment thereof with reference to the accompanying drawings.

Figure 1:
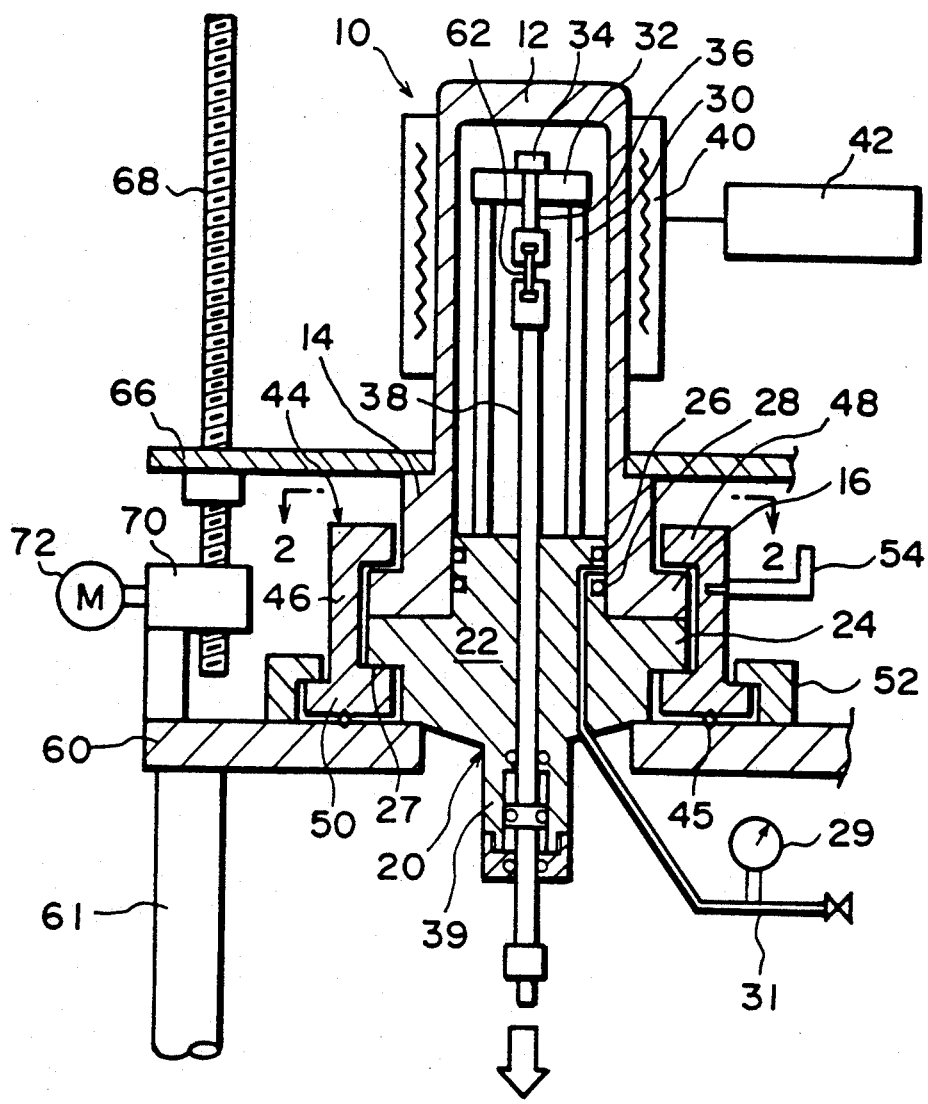
FIG. 1 is an elevational sectional view of a sealing structure for a testing vessel, according to a preferred embodiment of the present invention.
Figure 2:
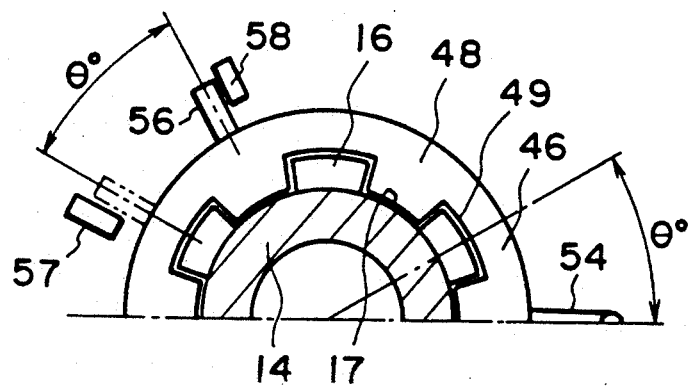
FIG. 2 is a sectional view taken along the line 2—2 in FIG. 1.

In FIG. 1, a testing vessel includes a cylindrical container 10 having an upper closed end 12 and a lower enlarged open end portion 14, and a plurality of radially extending locking portions 16 and a plurality of notches 17 are alternately formed on the enlarged end portions within a predetermined angular range (refer to FIG. 2). A lid member 20 secured to a base 60 has an insertion portion 22 adapted to be inserted into the enlarged end portion 14, and a supporting portion 24 having the same diameter as those of the locking portions 16. A passage 31 extends from an inner space between the enlarged end portion 14 and the insertion portion 22, and a pressure gauge 29 is disposed in the passage to measure the pressure in the inner space. Further, a pair of upper and lower seal members 26, 28 are arranged between the enlarged end portion 14 and the insertion portion 22.

An appropriate number of lead supporting rods 30 are arranged within the container 10 in such a manner that lower ends of the rods are supported by an upper surface of the lid member 20, and upper ends of the rods are interconnected by a support plate 32. A rod 36 is attached to the support plate 32, which rod is connected to another rod 38 via a test piece. The rod 38 extends downwardly through the lid member 20, and a lower end of this rod is connected to a tensioning device (not shown). A heater 40 is disposed around the periphery of the container 10 and a temperature of the heater is controlled by a temperature adjuster 42. A lower portion of the rod 38 is sealed by a sealing device 39.

A clutch member 44 is disposed around the enlarged end portion 14 and locking portions 16 of the container 10 and around the supporting portion 24 of the lid plate 20. The clutch member 44 comprises a cylindrical portion 46 on an upper end of which a plurality of locking portions 48 and notches 49 are alternately formed within the same angular range as that of the locking portions 16 of the container. A sliding portion 50 is formed on a lower end of the clutch member 44 to extend radially. An inner peripheral portion of the sliding portion 50 is housed in an annular recess 27 formed in the supporting portion 24, and an outer peripheral portion of the sliding portion is positioned and guided by a guide member secured to a base 60. A bearing 45 is disposed between the sliding portion 50 and the base 60.

A rod 54 extends radially outwardly from the clutch member 44, which rod is driven in an circumferential direction by means of a manipulator or a drive means (not shown). When the locking portions 48 are aligned with the locking portions 16, the container 10 cannot be dismounted from the lid plate 20; whereas, when the locking portions 48 are not aligned with the locking portions 16, the container can be dismounted from the lid plate.

Incidentally, as shown in FIG. 2, the rotation of the clutch member 44 is limited to a certain extent by abutting a rod 56 secured to the clutch member against either one of a pair of stoppers 57, 58. Further, an elevator plate 66 secured to the enlarged end portion 14 of the container 10 is threadedly engaged by a threaded rod 68, so that the container 10 is mounted on or dismounted from the lid plate 20 by lowering or lifting the elevator plate 66 by rotating the threaded rod 68 by means of a motor 72 via a jack 70.

Next, the operation of the sealing structure according to the illustrated embodiment will be explained.

When the container 10 is dismounted from the lid plate 20 to set the test piece 62 within the testing vessel or remove the test piece from the testing vessel, the clutch member 44 is rotated in a circumferential direction by a predetermined angle θ via the manipulator until the rod 56 is abutted against the stopper 57. In this case, the clutch member 44 can be rotated with a small force because of the provision of the bearing 45 and the guide member 52. During the rotation of the clutch member 44, when the locking portions 48 are aligned with the notches 17, the elevator plate 66 is lifted, with the result that the container 10 is shifted upwardly to be separated from the lid plate 20.

When the container 10 is attached to the lid plate 20, a reverse operation is effected. That is to say, after the container 10 is rested on the lid plate 20 by lowering the elevator plate 66, the clutch member is rotated in the circumferential direction via the manipulator until the rod 56 is abutted against the stopper 57. Consequently, the locking portions 48 are aligned with the locking portions 16 so that the locking portions 16 are positioned below the locking portions 48, thus preventing the separation of the container 10 from the lid plate 20.

In this condition, a temperature in the container 10 is increased up to a predetermined value by adjusting the heater 40 and a pressure in the container 10 is adjusted to a predetermined value by a pressure adjusting means (not shown). The sealing condition between the container 10 and the lid plate 20 is ensured by the first and second seal members 26, 28.

Thereafter, a downwardly directing force is applied to the rod 38. Thus, by measuring the tensile load, a time until the test piece 62 is broken, a dimension of the test piece and the like, it is possible to analize the property of the test piece under the high temperature and high pressure.

With this arrangement, since the rotation of the clutch member 44 is effected via the manipulator, even if the condition within the container 10 is radioactive, the operator is not exposed to the dangerous atmosphere. Further, since the container 10 is lifted and lowered by means of the elevator plate 66, motor 72 and the like, the operator does not need to monitor and/or adjust the movement of the container 10 at its side.

Incidentally, while the present invention was explained in connection with the preferred embodiment thereof, it is not limited to the illustrated embodiment, and therefore, it should be noted that any alterations or modifications can be adopted without departing from the spirit and scope of the present invention.

What is claimed is:

1. A sealing structure for a testing vessel, comprising:
a fixed lid member secured to a base and having an upwardly projecting insertion portion and a supporting portion;
a cylindrical container detachably mountable on said lid member in an up-and-down direction, said container having a lower open end portion to which said insertion portion can be mated and which can be supported by said supporting portion and on which a plurality of first radially outwardly extending locking portions and first notches are alternately formed along a circumference thereof;
a clutch member which is attached to said base and rotatingly guided in a circumferential direction by a guide member and on which a plurality of second radially inwardly extending locking portions and second notches are alternately formed within the same angular range as that of said first locking portions and first notches; and
an elevator means for lowering and lifting said container to mount and dismount the latter with respect to said lid member;
wherein when said first and second locking portions are aligned with said second and first notches by rotating said clutch member, said container can be mounted on or dismounted from said lid member by lowering or lifting said container by means of said elevator means, and said container is nondetachably attached to said lid member when said first locking portions are engaged by said second locking portions.

* * * * *